United States Patent [19]

Jensen

[11] Patent Number: 4,810,496
[45] Date of Patent: Mar. 7, 1989

[54] TREATMENT OF SKIN AND INFLAMMATORY DISORDERS

[76] Inventor: Charles A. Jensen, 401 E. California Blvd., Pasadena, Calif. 91106

[21] Appl. No.: 822,532

[22] Filed: Jan. 27, 1986

Related U.S. Application Data

[63] Continuation-in-part of Ser. No. 702,946, Feb. 17, 1985, abandoned.

[51] Int. Cl.$^4$ ...................... A61K 33/00; A61K 33/08
[52] U.S. Cl. .................................... 424/127; 424/157; 424/166; 514/859; 514/863; 514/947
[58] Field of Search ................. 424/157, 127; 514/947

[56] References Cited

U.S. PATENT DOCUMENTS 3,137,622  6/1964  Mueller et al. ................. 424/157 X

OTHER PUBLICATIONS

Kirk-Othmer—"Encyclopedia of Chemical Technology", vol. 5, 1964, pp. 541–554, 580 & 581.

*Primary Examiner*—Leonard Schenkman
*Attorney, Agent, or Firm*—Nixon & Vanderhye

[57] ABSTRACT

A method of treating skin disorders, inflammatory conditions and certain internal infections and disorders by administering, either externally by topical application or internally through oral ingestion, an effective amount of a mixture of mineral compounds in appropriate parts by weight of aluminum oxide hydrate, iron, magnesium oxide, silicon dioxide, sodium hydroxide and potassium hydroxide, along with trace amounts of copper, zinc, and calcium, with the balance of the mixture comprising ammonium sulfate or, in the case of topically applied formulations, a pharmaceutically acceptable carrier or diluent.

13 Claims, No Drawings

TREATMENT OF SKIN AND INFLAMMATORY DISORDERS

This application is a continuation-inpart of my earlier application Ser. No. 702,946, filed Feb. 17, 1985, now abandoned.

The present invention relates to the treatment of various disorders of the skin, including fungal infections, as well as to the treatment of certain inflammatory and internal disorders and infections. More particularly, it relates to the treatment of skin, inflammatory and internal disorders through the use of a topically applied or orally ingested pharmaceutical composition comprising a mixture of aluminum, iron, magnesium and other mineral compounds.

The following skin disorder may be treated in accordance with the present invention: psoriasis, dermatitis, dandruff, eczema, ichthyosis, athlete's foot, acne, fungus infections, scabies, skin rashes, scleroderma, moles/warts and cysts. Superficial fungal infections of the skin, toe nails and finger nails may also be treated.

Inflammatory disorders, which may be treated with compositions according to the invention may share common features with one or more of the skin disorders listed above and include hemorrhoids, inflammatory dermatoses and similar conditions.

Specific skin disorders and inflammatory conditions treated are illustrated by the following non-exhaustive list:

Cysts—abnormal sacs containing a gas, fluid or semi-solid material including cysts of the dermis such as epidermal cysts of the inclusion or implantation type;

Dermatitis—an inflammation of the skin caused by many sources including skin sensitivity to light (sunlight), chemicals, perfumes, allergies to various plants and animals including contact type dermatitis, exfoliative, seborrheic dermatosis or eczema;

Hemorrhoids—a varicose condition of the external hemorrhoidal veins causing painful swellings at the anus, both internal, when the swollen veins are beneath the mucous membrane within the external sphincter, and external when the dilated veins form tumors to the outer side of the sphincter;

Moles—including benign intradermal nevi and compound nevi;

Psoriasis—a condition characterized by the eruption of circumscribed, discrete and confluent silver scaled skin occurring primarily on the elbows, knees, scalp, and trunk.

Superficial fungal infections treated in accordance with the invention include ringworm (tinea) of various body parts including nails, scalp, groin, beard and feet (athlete's foot).

Conventional regimens of therapy have dealt with many of these conditions in a variety of ways, e.g., surgically, topically and systemically. For a summary of such approaches, see *The Merck Manual*, 14th Edition (1982). The methods and compositions of this invention represent a marked departure from these prior treatments.

Pharmaceutical presentation—The compositions of the invention may be administered in any convenient topical, oral or rectal form in suitable pharmaceutical vehicle or as a powder. Suitable pharmaceutical vehicles are well known in the art according to the type of preparation desired. Thus, for example, tablets capsules, ingestible liquids or powder preparations, topical liquids and powder preparations, creams, ointments, salves, lotions for topical application and suppositories can be prepared as required. The optimum pharmaceutical presentation is conveniently determined empirically by one skilled in the art of compounding pharmaceutical preparations.

Also included within the presentations contemplated by this invention are dietary mineral supplements to be taken by the patient to supplement his/her daily mineral intake. Such presentations typically take the form of orally-ingested preparations such as tablets and capsules.

It will be understood that because the elements present are not toxic the absolute quantity of active ingredients present in any dosage unit or unit of application may or may not exceed that appropriate to the rate and manner of administration to be employed and should desirably be adequate to allow the intended rate of administration to be achieved by a larger or smaller number of doses or applications. The rate of administration will, moreover, depend on the condition being treated, the form of pharmaceutical presentations(s) employed, and the precise pharmacological action desired.

Veterinary formulations and presentations are also included within the scope of the present invention, and in addition to the presentations noted above intended primarily but not exclusively for human use, suitable formulations include feed supplements and additives, chewable flavored tablets and capsules. A preferred form is to blend the compound of aluminum, iron, magnesium and other elements with the animal's food for administration in the form of a mash, pellet, granule or other convenient style, Vitamins, minerals, antibiotics, antioxidants, and other pharmacologically active compounds of the type contained in domestic animal feeds may also be included.

The essential component of the pharmaceutical compositions and methods of treatment herein described is a mineral compound and inorganic oxides containing principally the oxides of aluminum and magnesium together with iron (believed to be in the form of iron hydroxide) with minor amounts of the oxides or hydroxides of silicon, sodium and potassium together with trace amounts of other elements such as calcium, zinc and copper. A more detailed analysis is given below.

The particular mixture of the inorganic mineral compound employed in my invention is isolated from a Nevada ore. Once removed from the ground the ore is crushed to a fine powder and sized, treated with a minor amount of sulfuric acid and heated to form a suspension. The pH is adjusted with a base such as ammonium hydroxide, filtered, dried and again pulverized. Complete details of treating the ore to give the desired product are given below.

X-Ray diffraction analysis and atomic absorption spectrometry define the composition as follows:

| Composition | Wt % |
| --- | --- |
| Ammonium Sulfate | 83.0 |
| Aluminum Oxide Hydrate Al(OH)$_3$ | 7.25 |
| Magnesium Oxide M$_g$O | 1.99 |
| Iron Fe | 3.33 |
| Silicon Dioxide SiO$_2$ | 0.62 |
| Sodium Hydroxide NaOH | 0.42 |
| Potassium Hydroxide KOH | 0.46 |
| Free Water @ 105° H$_2$O | 2.53 |

Trace amounts of calcium, zinc and copper were detected. Proportions of the various ingredients may vary ±% of the value stated. That is, the precise values given above may vary up to ±1.5% for the aluminum and magnesium oxides and iron and ±0.5% for the remaining oxides and hydroxides present. A preferred material is a mixture of the following, expressed in parts by weight:

| | |
|---|---|
| aluminum oxide hydrate | about 18 parts |
| iron | about 11 parts |
| magnesium oxide | about 5 parts |
| silicon dioxide | about 1.5 parts |
| sodium hydroxide | about 1 part |
| potassium hydroxide | about 1 part | including trace amounts of copper, zinc, and calcium, with the balance of the mixture comprising ammonium sulfate. The mixture may be used by itself or with a suitable pharmaceutical vehicle, as discussed below. Unless otherwise indicated, all parts and percentages given throughout this specification and in the appended claims are by weight and all temperatures are reported in degrees F.

Preparation Of The Inorganic Mineral Powder

The following is a typical procedure for preparing the inorganic mineral powder used in the present invention:

1. The inorganic mineral powder is extracted from ore in a Plaster mining claim in Nevada. After removal of two feet of overburden, the ore is removed by excavation and run through a jaw crusher which evens out the mesh size and removes lumps which are present.
2. The ore is then pulverized and the mesh size further reduced to at least minus forty mesh (Tyler) screen.
3. A solution composed of 14% $H_2SO_4$ and 85% water (deionized) is mixed together in a vessel, i.e., a Pfaudler tank. Water from the water table below the surface of the mining claims is acceptable and can be used. After this is done, the fine ore is added to this solution at a ratio of 1.5 pounds of ore for each 1.8 liters of solution. This ratio of ore to solution can be used up to any volume, limited only by the size of the vessel being used. Heating, pressurizing and agitating the contents of the treatment vessel shortens recovery time.
4. The aqueous ore mixture is then heated to a minimum of 250° F. to suspend the ore until the ore "pump" turns to a light buff color. A scan can also be taken to assure that all of the elements to be recovered have been placed into suspension. Agitation of the ore in solution will speed up the process of placing the elements into suspension. However, this is not a requirement needed for successful recovery of the final product.
5. After the elements are in suspension, the heat is turned off and the solution containing the elements in suspension and the pulp, which will drop to the bottom of the container, is allowed to cool and stand overnight.
6. Separation of the solution from the pulp is then achieved by filtration, using No. 541 filter paper. Other filtration may also be used.
7. Ammonium hydroxide ($NH_4OH$) 26°Baume is then carefully added to the solution, using MAG-MIX; the solution is stirred during this addition to avoid generating too much heat or nay other unfavorable reaction. While this is being done, a pH probe is placed into the solution from time to time to maintain the pH between 7.5 and 8.0 but never below 7.5. The precipitate will have a rich brown color if all prior steps have been properly taken.
8. The solution is allowed to stand for a minimum of four hours and preferably overnight. The solution is then at ambient temperature and is again filtered, using No. 541 filter paper.
9. After removing the product from the filter paper into a clean heat resistant (PYREX) container of flat, rectangular shape, spreading the product evenly to allow uniformity in drying, the container is placed in an oven dryer at 255° F. until the product is dry. A rotary dryer could also be used.
10. After drying, the product should be placed in closed container (desiccator) to prevent adsorption of moisture from air to eliminate lumping, the material is run through a plate pulverizer to -100 mesh (Tyler) which makes the product easy to place the capsules or mix with an emollient base for different types of pharmaceutical presentations.

General Methods of Use—One of the formulations described above is applied to the affected area, when topical application is indicated, and then allowed to remain in contact, often with the aid of a dressing or bandage, until the symptoms have improved. For hemorrhoids or other inflammatory conditions in the anorectal area a petroleum-based ointment or paste is applied or a suppository is inserted. For psoriasis, dermatitis, moles and cysts a water-soluble cream base allows the preparation to blend into the skin is desirable. Moles, cysts and fungus infections particularly in the toenail and fingernail area are advantageously treated with a petroleum-based ointment. Powders in accordance with the present invention are conveniently dusted onto the desired area while capsules and tablets are taken orally.

Ointment bases suitable for preparing topically applied pharmaceutical preparations according to the invention are selected from the oleanginous bases, and which include animal and plant fats, petroleum hydrocarbons and silicones, absorption bases, emulsion bases, water-soluble bases. Suitable ointment bases and procedures for ointment preparation are described in *Remington's Pharmaceutical Sciences* pp. 525-543, Mack Publishing Co. (1965).

The invention is further illustrated with reference to the following pharmaceutical formulations:

Ointment

Equal quantities of the inorganic mineral powder are mixed with Aloe Vera Gel or with a petroleum jelly (Vasoline) base using a steel spatula and glass ointment slab to make a smooth, semi-translucent ointment.

Cream

Equal quantities by weight of the inorganic mineral powder are mixed with Dermabase cream base using a spatula and ointment slab to make a smooth light brown, creamy ointment that upon application with rubbing is absorbed into the skin.

Powders

The inorganic minerals are finely ground and sized into a free-flowing powder which is packaged in 4 oz.

shaker containers suitable diluents and desicants may be included as required.

Capsules

Gelatin capsules, ranging from size 00 to number 4 are filled with powdered inorganic minerals, a diluent being included as desired to adjust the active ingredient content per capsule.

The following examples will serve to illustrate pharmaceutical compositions and methods of treatment in accordance with the present invention:

EXAMPLE 1

Treatment of Hemorrhoids

A topical cream was prepared using the mineral compound distributed in an emollient base. The paste contained the following ingredients by weight percent

| Ammonium Sulfate | 41.5 |
| --- | --- |
| Aluminum Oxide Hydrate | 3.63 |
| Magnesium Oxide | 1.0 |
| Iron | 1.67 |
| Silicon Dioxide | 0.31 |
| Sodium Hydroxide | 0.21 |
| Potassium Hydroxide | 0.23 |
| Free Water @ 105° F. | 2.26 |
| Emollient Base | 50.00 |

EXAMPLE 2

A patient who had experienced acutely inflammed internal and external hemorrhoids was provided with the paste as described in Example 1 with instructions to apply the paste topically daily to the affected area. At the end of 4 weeks the itching and pain previously associated with the involved rectal tissue had subsided and the swollen tissue was reduced about 75% in size.

EXAMPLE 3

Treatment of Rectal Fissures

A patient having a history of bleeding rectal fissures for the previous 2-3 years was given the paste as prepared in Example 1 with instructions to apply the paste topically to the affected area once a day and to continue the application until symptoms improved. At the end of 10 days the patient reported a 90% reduction in the bleeding and continued treatment resolved the symptoms.

EXAMPLE 4

Treatment of Tinea Pedis

A man with a long standing fungal infection (Athlete's Foot) of the left foot and toenail intermittently self treated his foot with all available therapies without success. Vesicles were observed on the left sole and a thickened, loosened medial half of the first toenail as noted. The left first toenail could easily be lifted away from the underlying skin.

An ointment was prepared of 50 parts by weight of the mineral powders described in Example 1 uniformly distributed in an equal quantity of petroleum jelly (Vasoline) base. The patient was given a supply of ointment and instructed to apply it to the toe and left foot areas followed by bandaging. The ointment remained in place 2-3 days then was removed with the dressing and the foot left untreated for 2 weeks. The procedure was repeated 4 more times.

When again seen by his dermatologist, the patient's left sole appeared to be free of abnormalities and his left first toenail was firmly attached. Cultures from the left foot and left first toenail on mycobiotic agar showed no growth. The patient had had no re-occurrence of the problem.

EXAMPLE 5

Treat of Psoriasis

A white male having a history of psoritic lesions on his extremities and groin for the previous 3 years was prescribed the ointment product prepared in Example 4. Four topical applications of the ointment preparation in accordance with Example 4 were made over a 2 week period. At the conclusion of therapy the psoritic lesion had healed to smooth, clear epidermal tissue.

EXAMPLE 6

Treatment of Moles

A patient was examined and a previously small mole on the forearm had become hyperplastic growing to about 3 times its original size. The mole's color changed from light brown to grey, and its texture from smooth to rough and granular. These changes occured over a period of about 60 days.

The ointment of Example 4 was applied once, topically and bandaged. Approximately 2 days later the are of the lesion was examined. The area was clear, previously fixed pathological tissue was completely removed, and the underlying smooth epidermal surface showed no evidence of inflammation or abnormality 24 hours after this single application.

EXAMPLE 7

Preparation of Capsules

Capsules for oral administration were prepared using an inorganic mineral powder containing the following ingredients:

| Composition | | % by Weight |
| --- | --- | --- |
| Ammonium Sulfate | $(NH_4)SO_4$ | 83.0 |
| Aluminum Oxide Hydrate | $Al(OH)_3$ | 7.25 |
| Iron | Fe | 3.53 |
| Magnesium Oxide | MgO | 1.99 |
| Silicon Dioxide | SiO | 0.62 |
| Sodium Hydroxide | NaOH | 0.42 |
| Potassium Hydroxide | KOH | 0.46 |
| Free Water @ 105° F. | $H_2O$ | 2.53 |

The mineral powder also contained trace amounts of copper, zinc and calcium

Size 4 capsules were filled with the above powder, each capsule containing 231.2 mg of the powder. No fillers, additives or diluents are used.

EXAMPLE 8

Treatment of Arthritis and Bursitis

A man suffering with chronic joint pain caused by bursitis and arthritis, unable to walk without the assistance of a cane, suffered pain and stiffness. His condition degenerated and over a period of time he was able to stand erect only for short periods of time.

The patient began taking the capsules of Example 7, six capsules per day. Positive results were noted in a few days and at the end of three weeks of therapy the patient was able to walk for distances of as much as half a mile without the use of a cane., an accomplishment the patient had not been able to do in the past 3 years. The patient reports no adverse effects and has reduced intake to three capsules per day.

What is claimed is:

1. A method of treating skin disorders comprising:
   administering to an animal or human having a skin disorder an effective amount of a mixture in percent by weight of:

| | |
   |---|---|
   | ammonium sulfate | about 83.0 |
   | aluminum oxide hydrate | about 7.25 |
   | iron | about 3.33 |
   | magnesium oxide | about 1.99 |
   | silicon dioxide | about 0.62 |
   | sodium hydroxide | about 0.42 |
   | potassium hydroxide | about 0.46 |
   | free water | up to 2.53 | including trace amounts of copper, zinc, and calcium, optionally with a pharmaceutically acceptable carrier or diluent.

2. The method according to claim 1 in which the inflammatory condition is inflammatory dermatoses.

3. The method according to claim 1 in which the skin disorder is psoriasis.

4. The method according to claim 1 in which the skin disorder is dermatitis.

5. The method according to claim 1 in which the skin disorder is acne.

6. The method according to claim 1 in which the skin disorder is a fungus infection.

7. The method according to claim 1 in which the skin disorder is tinea pedis.

8. The method according to claim 1 in which the skin disorder is tinea unguium.

9. The method according to claim 1 in which the skin disorder is a nevus.

10. The method according to claim 1 in which the skin disorder is a cyst.

11. A method of treating an inflammatory condition comprising:
    administering to an animal having an inflammatory condition, an effective amount of the mixture, in percent by weight of:

| | |
    |---|---|
    | ammonium sulfate | about 83.0 |
    | aluminum oxide hydrate | about 7.25 |
    | iron | about 3.33 |
    | magnesium oxide | about 1.99 |
    | silicon dioxide | about 0.62 |
    | sodium hydroxide | about 0.42 |
    | potassium hydroxide | about 0.46 |
    | free water | up to 2.53 | including trace amounts of copper, zinc, and calcium, optionally with a pharmaceutically acceptable carrier or diluent.

12. A method of treating hemorrhoids comprising:
    topically applying to the affected hemorrhoid tissue of an animal suffering therefrom an effective amount of the mixture in percent by weight of:

| | |
    |---|---|
    | ammonium sulfate | about 83.0 |
    | aluminum oxide hydrate | about 7.25 |
    | iron | about 3.33 |
    | magnesium oxide | about 1.99 |
    | silicon dioxide | about 0.62 |
    | sodium hydroxide | about 0.42 |
    | potassium hydroxide | about 0.46 |
    | free water | up to 2.53 | including trace amount of copper, zinc, and calcium, optionally with a pharmaceutically acceptable carrier or diluent.

13. A pharmaceutical composition comprising as the active therapeutic ingredient a mixture, in percent by weight, of:

| | |
    |---|---|
    | ammonium sulfate | about 83.0 |
    | aluminum oxide hydrate | about 7.25 |
    | iron | about 3.33 |
    | magnesium oxide | about 1.99 |
    | silicon dioxide | about 0.62 |
    | sodium hydroxide | about 0.42 |
    | potassium hydroxide | about 0.46 |
    | free water | up to 2.53 | including trace amount of copper, zinc, and calcium, together with a pharmaceutically acceptable non-aqueous carrier.

* * * * *